(12) United States Patent
Golova et al.

(10) Patent No.: US 7,705,136 B2
(45) Date of Patent: Apr. 27, 2010

(54) SYNTHESIS OF 3'-, OR 5'-, OR INTERNAL METHACRYLAMIDO-MODIFIED OLIGONUCLEOTIDES

(75) Inventors: Julia B. Golova, Willowbrook, IL (US); Boris K. Chernov, Willowbrook, IL (US)

(73) Assignee: UChicago Argonne, LLC, Chicago, IL (US)

( * ) Notice: Subject to any disclaimer, the term of this patent is extended or adjusted under 35 U.S.C. 154(b) by 1238 days.

(21) Appl. No.: 11/066,791

(22) Filed: Feb. 25, 2005

(65) Prior Publication Data

US 2006/0194213 A1 Aug. 31, 2006

(51) Int. Cl.
*C07H 21/00* (2006.01)
*C07H 21/04* (2006.01)
*C12Q 1/68* (2006.01)
*C40B 50/00* (2006.01)
*C07C 237/00* (2006.01)

(52) U.S. Cl. .......... 536/23.1; 536/25.3; 435/6; 506/23; 564/204; 977/792

(58) Field of Classification Search .......... 435/6; 536/23.1, 25.3; 506/23; 564/204; 977/792
See application file for complete search history.

(56) References Cited

U.S. PATENT DOCUMENTS

2004/0086866 A1 5/2004 Chernov

FOREIGN PATENT DOCUMENTS

RU 2175972 9/2001
WO WO 03/010203 7/2001

OTHER PUBLICATIONS

Claus B. V. Christensen, (2002) Arrays in biological and chemical analysis, Talanta, vol. 56, Issue 2, , pp. 289-299.
Rubina et al., (2004) Hydrogel drop microchips with immobilized DNA: properties and methods for large-scale production. Anal Biochem.; 325(1):92-106.
Vasiliskov V.A. et al., (1999) Fabrication of microarray of gel-immobilized compounds on a chip by copolymerization. Biotechniques.; 27(3):592-4, 596-8, 600.
Farah, N. et al. (1999) Nucleic Acids Res., 27, 649-655.
Roland et al., (2001) A novel linker for the solid-phase synthesis of a library of 3'—thiophosphorylated dinucleotides , Tetrahedron Letters, vol. 42, Issue 22, pp. 3669-3672.

*Primary Examiner*—Jezia Riley
(74) *Attorney, Agent, or Firm*—Barnes & Thornburg LLP; Alice O. Martin

(57) ABSTRACT

New modifiers were synthesized for incorporation of a methacrylic function in 3'-, 5'- and internal positions of oligonucleotides during solid phase synthesis. A modifier was used for synthesis of 5'-methacrylated oligonucleotides for preparation of microarrays by a co-polymerization method.

20 Claims, 5 Drawing Sheets

SYNTHESIS OF 3'-, OR 5'-, OR INTERNAL METHACRYLAMIDO-MODIFIED OLIGONUCLEOTIDES

This invention was partially conceived under Contract No. W-31-109-ENG-38 between the US Department of Energy and The University of Chicago representing Argonne National Laboratory.

BACKGROUND

DNA-based microarrays are important for various applications regarding nucleic acid analyses, such as the monitoring of mRNA expression, the sequencing of DNA fragments, genotyping and diagnoses of single-nucleotide polymorphisms, detection of viruses and other pathogens. A co-polymerization method is one of the most progressive technologies for manufacturing three-dimensional (3D) DNA microarrays also called biochips. In this method oligonucleotide probes are mixed with acrylamide or methacrylamide, applied as a spot on a glass slide and then allowed to polymerize under UV-exposure forming a biochip. The co-polymerization method needs oligonucleotide probes to be modified with functional groups containing unsaturated C=C bonds able to copolymerize with gel forming monomers. Matrix Technology Corporation, US, produces Acrydite™ amidite and Dimethoxytrityl-acrydite™ amidite for incorporation of an acrylic function into oligonucleotides during solid phase synthesis. But a methacrylamide group is reported to be preferable in this technology because it is more stable to spontaneous polymerization and demonstrates high efficiency of copolymerization with acrylamide and methacrylamide gel monomers. Modifiers containing a methacrylic function are reported.

SUMMARY

A new structure of methacrylate containing modifiers is used for oligonucleotide synthesis. The compositions described herein can be used for modification of any compound containing free hydroxyl and amino functions for solid-phase synthesis as well as synthesis in solutions. New modifiers were synthesized for incorporation of a methacrylic function in 3'-, 5'- and internal positions of oligonucleotides during solid phase synthesis. A modifier was used for synthesis of 5'-methacrylated oligonucleotides for preparation of microarrays by a co-polymerization method.

The disclosed structure and scheme of synthesis of novel methacrylic modifiers can be used for oligonucleotide modification during solid phase synthesis. This type of modified oligonucleotide is used for manufacturing of biochips by a new progressive co polymerization method. Thus, creation of new modifiers, which are used in frames of standard phosphoramidite reaction cycles during automated solid phase oligonucleotide synthesis, is useful for synthesis of methacrylated oligonucleotides.

A compound of the formula

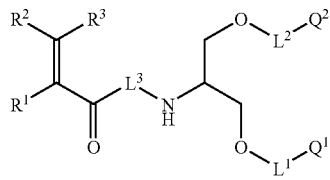

is described wherein $R^1$, $R^2$, and $R^3$ are each independently selected from the group consisting of hydrogen, alkyl;

$L^1$, $L^2$, and $L^3$ are each independently selected from the group consisting of a single bond, and a linker; and $Q^1$ and $Q^2$ are each independently selected from the group consisting of hydrogen, oxygen protecting groups, phosphoramidite group, oligonucleotides, solid supports, and combinations thereof.

$R^1$ is hydrogen or alkyl; and $R^2$ and $R^3$ are each hydrogen.

$L^3$ is a linker selected from the group consisting of co-amino acid fragments of the formula —NH—$(CH_2)_n$—CO— wherein n is integer from 2 to about 12.

$Q^1$ is an oligonucleotide attached at the 5'-end $Q^2$ is an oligonucleotide attached at the 3'-end $Q^1$ and $Q^2$ are each an independently selected oligonucleotide.

$Q^1$ is an oligonucleotide attached at the 5'-end and $Q^2$ is an oligonucleotide attached at the 3'-end.

$L^2$ is a single bond; and $Q^2$ is an hydroxyl protecting group.

The hydroxyl protecting group is an optionally substituted trityl group.

$L^1$ is a linker formed from a dicarbonic acid fragment.

For example, in FIG. 2, compound (I): R1, R2=hydrogen, R3=methyl (alkyl); L1=single bond or or CO(CH2)2CO, L2=single bond, L3=single bond or CO(CH2)5CO; Q1=solid support, Q2=hydroxyl protected group; for Compound (II): R1, R2=hydrogen, R3=methyl (alkyl), L1=single bond, L2=single bond, L3=single bond or CO(CH2)5CO; Q1=phosphoramidite group, Q2=hydroxyl protected group.

The dicarbonic acid fragment is an aliphatic diacid of the formula:

wherein m is an integer from 0 to about 8.

$L^1$ is a linker formed from a dicarbonic acid fragment; and $Q^1$ is a solid support A reagent for forming a compound of any one of the formulas above has the formula

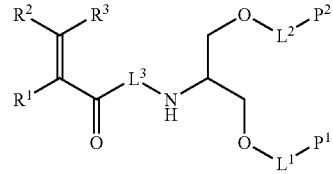

wherein $R^1$, $R^2$, and $R^3$ are each independently selected from the group consisting of hydrogen, alkyl;

$L^1$, $L^2$, and $L^3$ are each independently selected from the group consisting of a single bond, and a linker; and $P^1$ and $P^2$ are each independently selected from the group consisting of hydrogen, a hydroxyl protecting group, a phosphoramidite group, an oligonucleotide, a solid support, and combinations thereof.

$P^1$ is a cyanoethylphosphoramidite group.

$P^1$ is a solid support.

$L^1$ is a linker; and $P^1$ is a solid support.

The linker is a fragment of aliphatic dicarbonic acid of the formula:

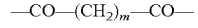

wherein m is an integer from 0 to about 8; and the linker is covalently attached to the solid support through a nitrogen of the amino group.

A method for preparing a biochip includes the steps of: placing a mixture comprising (i) an oligonucleotide of any one of the compounds described herein, or an analog or derivative thereof, and (i) a gel forming monomer e.g., an acrylate monomer, on a solid support; and polymerizing the mixture.

The acrylate monomer is an acrylamide. The placing step includes placing the mixture on the solid support in the form of a drop.

DEFINITIONS and ABBREVIATIONS

Array, microarray: a predetermined arrangement of molecules relative to each other connected to a support, also referred to as a chip, DNA chip, DNA microarray, DNA array, microchip, peptide chip, or peptide array. Illustratively, the array is a predetermined arrangement of biological molecules such as DNA fragments, peptides, proteins, lipids, drugs, affinity ligands, and the like.

Biochip: also known as a chip, DNA chip, DNA microarray, microchip, peptide chip or peptide array; includes array of biological molecules such as DNA fragments, peptides, proteins, lipids, and tissues connected to a matrix (small flat support).

CPG: control pore glass or controlled pore glass.

DMTr: 4,4'-dimethoxytrityl protecting group.

DNA: deoxyribonucleic acid

HPLC: high pressure liquid chromatography.

Linker: a polyfunctional molecule containing functional groups that may provide connection of different parts in the chemical structure oligonucleotide synthesis, e.g. control pore glass.

Modifier: a chemical that provides at least one functional amino group to a molecule, illustratively an oligonucleotide.

MALDI-TOF MS: matrix-assisted laser desorption/ionization time-of-flight mass spectrometry.

MW: molecular weight.

NOS: N-hydroxysuccinimidyl.

Oligomer or oligonucleotide: A nucleotide sequence (DNA or RNA) having about 6 or more nucleotides, and illustratively in the range from about 6 to about 100 nucleotides.

Phosphoramidite: phosphoramide derivatives of nucleosides used in chemical solid phase oligonucleotide synthesis.

Solid support: carrier for automated solid phase g-chain control pore glass.

TEAA: triethylammonium acetate buffer.

UV: ultraviolet.

DETAILED DESCRIPTION

New modifiers and methods of synthesis of the new modifiers for incorporation of a methacrylic group at the 3'-, 5'-termini or internal positions of immobilized oligonucleotide probes are described.

Modifiers are synthesized for incorporation of a methacrylic function in DNA probes to be used in the production of microchips (biochips) by co-polymerization method or for synthesis in solution.

In this method a oligonucleotide probe is mixed with an acrylamide or methacrylamide mixture, applied as a spot on the glass slide and then allowed to polymerize, forming a 'pre-loaded' biochip.

This co-polymerization procedure utilizes oligonucleotides that have functional groups containing unsaturated C=C bonds, which are able to interact with the gel forming monomers during polymerization. This type of oligonucleotide (oligos) can be generated by a post-synthesis procedure; however it is more desirable to produce such oligos during the automated solid phase synthesis.

New modifiers are synthesized that enable the incorporation of the methacrylic groups at either the 3'- or 5'-termini. The modifiers can also be internal to an oligo. (FIG. 1)

A copolymerization procedure is used for manufacturing a new type of three-dimensional semispherical biochips. In this approach immobilized oligonucleotides are supplied with functional groups containing unsaturated C=C bonds, which are able to participate in the polymerization process with gel forming monomers (usually, acrylamide or methacrylamide). These kinds of modified DNA probes can be obtained using a post-synthesis modification procedure as well as in the process of automated solid phase oligonucleotide synthesis. The special modifiers to be used in solid phase synthesis should contain unsaturated functional groups stable at the conditions of the oligonucleotide synthesis and following deprotection procedures. A methacrylic group fulfills these requirements: it is more stable to spontaneous polymerization and demonstrates high efficiency of copolymerization with acrylamide and methacrylamide gel monomers. Thus, a methacrylic group was used for obtaining modifiers containing unsaturated C=C bond.

Figure 2:
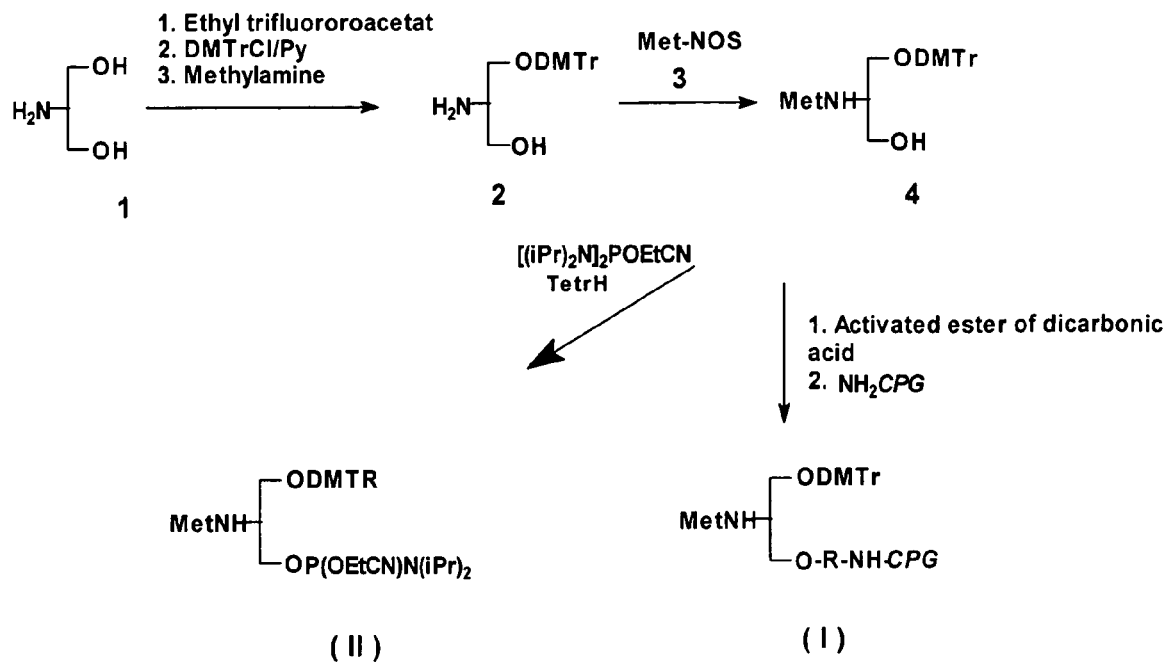
FIG. 2 shows an illustrative chemical synthesis of embodiments of methacrylamido modifiers (I) and (II) for incorporation of methacrylamide group at 5'-, 3'-termini or at internal position of oligonucleotide chain.
Figure 3:
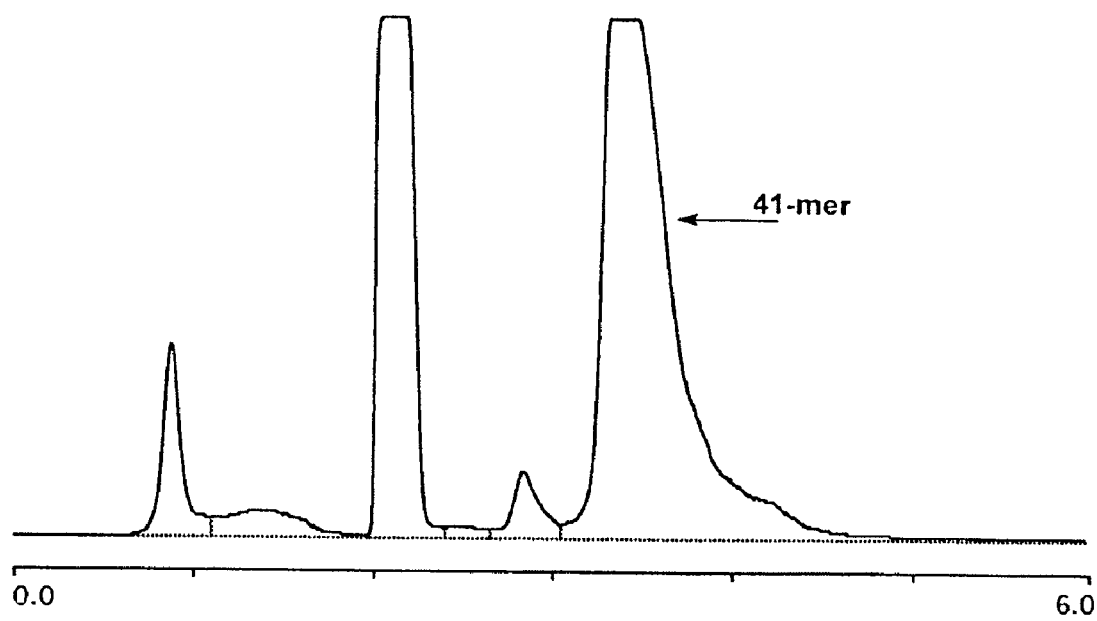
FIG. 3 shows a reversed-phase HPLC profile of isolation of a 5'-methacrylated 41-mer oligonuclotide from a crude reaction mixture (column RPR-1, 7×100 mm, gradient of acetonitrile (20-50%) in 0.05M TEAA, flow 2.5 ml/min, UV detection at 285 nm).
Figure 4:
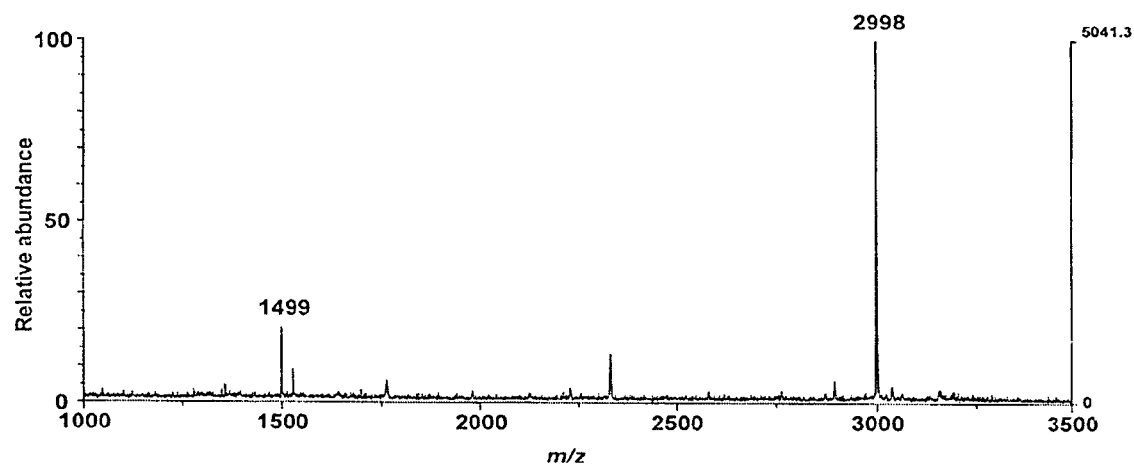
FIG. 4—shows MALDI TOF mass spectrum of 5'-methacrylated 9-mer oligonucleotide TAACTTCAT (theoretical MW=2997).
Figure 5:
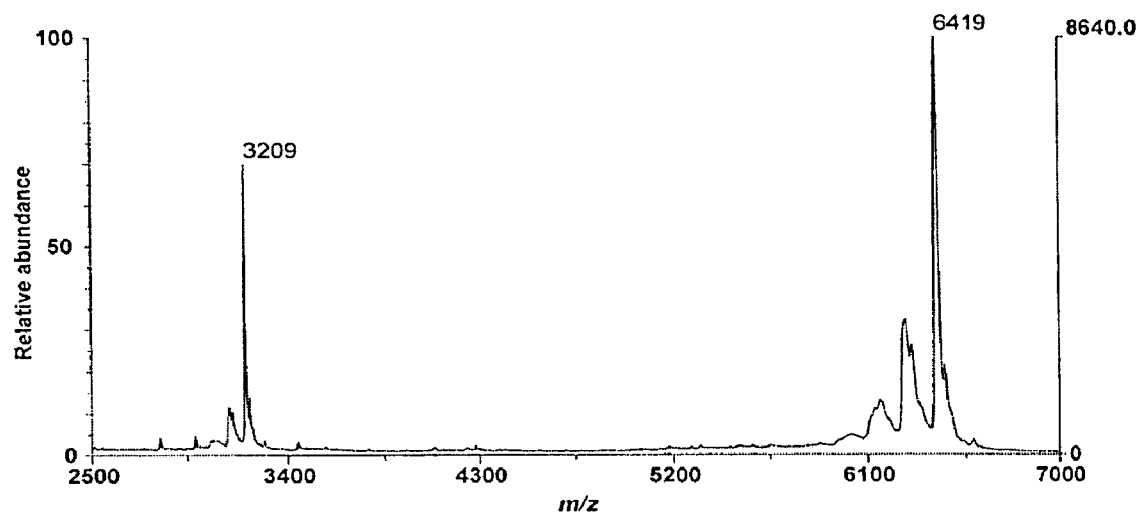
FIG. 5 shows MALDI TOF mass spectrum of 3'-methacrylated 21-mer oligonucleotide TAACTTCATAAGAG-CAAGCCT (SEQ ID NO: 1) (theoretical M W=6420).

FIG. 2 shows the chemical synthesis of two kinds of modifiers starting from 1-O-DMTr-serinol obtained as described in US Patent Application Publication 2004/0086866A1, which included sequential reactions of serinol with ethyl trifluoroacetate and 4,4'-dimethoxytritylchloride followed by treatment of methylamine. The reaction of mono-protected serinol (2) with activated ester of methacrylic acid or its derivative (3) gives compound (4). Further connection of synthon (4) to controlled pore glass (CPG) using activated ester of dicarbonic acid gives modifier (I). Phosphitilation of synthon (4) with 2-cyanoethyl diisopropylphosphoroamidite leads to formation of modifier (II).

Figure 1:
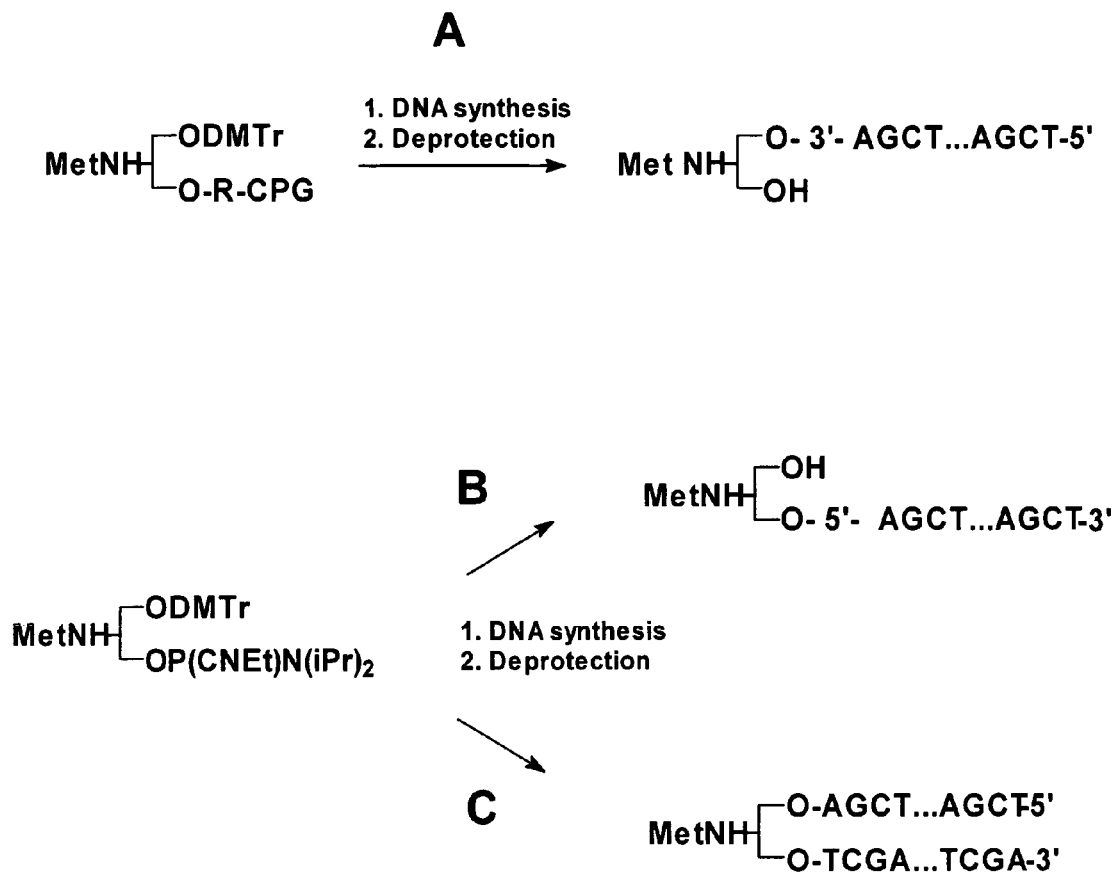
FIG. 1 shows possible ways for incorporation of a methacrylamide group at 3' (A) and 5' (B)-termini or at internal position (C) of an oligonucleotide chain.

Methacrylamido-modifier (I) is used as a support for automated solid phase oligonucleotide synthesis and provides the introduction of methacrylic group at the 3'-terminus of synthesized probe(s) after complete elongation of oligonucleotide chain and deprotection procedure (FIG. 1, A). Modifier (II) is used on the last step of solid phase synthesis (FIG. 1, B) renders the incorporation of methacrilyc function at the 5'-terminus of the sequence. While used at the middle of synthesis the same modifier (II) allows the creation of double-stranded oligonucleotide probe supplied with methacrylic function (FIG. 1, C).

Described compounds (I) and (II) were used for synthesis of 3'- and 5'-modified oligonucleotides. Methacrylated oligonucleotides were successfully applied as immobilized probes in manufacturing of hybridization biochips for detection and identification of microorganisms.

MATERIALS AND METHODS

Synthesis of Methacrylamido-modifiers (I) and (II), FIG. 2

1. 1-O-4,4'-dimethoxytrityl-serinol (2)—Synthesis of 1-DMTr-serinol was performed as described in [7]

2. N-hydroxysuccinimidyl-N-methacryloyl-6-aminocaproic acid (3, Met=b, n=2).

A. To a solution of 6-aminocaproic acid (6.55 g, 50 mmol) in 150 ml of glacial acetic acid methacrylic anhydride (8.7 ml, 55 mmol) were added at room temperature, and resulting mixture was stirred for 12 hours. All volatiles were removed under reduced pressure. Crude material was submitted to column chromatography on silica gel, which was performed in chloroform with applying gradient of methanol (0-7.5%) and gave 8.65 g (87%) of N-methacryloyl-6-aminocaproic acid as white solid. MALDI MS: found 200.06 (M+H)$^+$, $C_{10}H_{17}NO_3$; calc. 199.07.

B. N-methacryloyl-6-aminocaproic acid (3.98 g, 20 mmol) was dissolved in 50 ml of acetone, and then to this solution 1,3-dicyclohexlylcarbodiimide (4.5 g, 22 mmol) and N-hydroxysuccinimide (2.55 g, 22 mmol) were added. Resulting mixture was stirred at room temperature for 6 hours. The reaction was quenched by addition of 1 ml of water, the precipitate of 1,3-dicyclohexylurea was removed by filtration and washed with acetone. The solution was concentrated in vacuum and purified by column chromatography on silica gel using step gradient of acetone (0-5%) in chlorophorm to give activated ester (3, Met=b, n=2) with yield 81% (4.8 g). MALDI MS: found 296.1, $C_{14}H_{20}N_2O_5$, calc. 296.09.

3. Methacrylated derivative of serinol (4, Met=b, n=2). To a solution of 1-DMTr-serinol (2) (1.96 g, 5 mmol) and triethylamine (0.7 ml, 5 mmol) in acetonitrile (15 ml) was added activated ester (3, Met=b, n=5) (1.2 g, 6 mmol) dissolved in 15 ml of acetonitrile. The resulting solution was stirred during 2 hours and then evaporated in vacuum. The residue was dissolved in ethyl acetate, organic phase was washed with water, dried with $Na_2SO_4$ and evaporated. Purification of the remaining oil by silica gel column chromatography using a step gradient of acetone (0-10%) in benzene afforded compound (4, Met=b, n=5) with yield 80% (2.3 g). MALDI MS: found 575.1, $C_{34}H_{42}N_2O_6$; calc. 574.28.

4. Methacrylamide modifier CPG (I; Met=b, n=5, m=2). To a solution of (4, Met=b, n=5) (575 mg, 1 mmol) in pyridine 95 ml) were added succinic anhydride (200 mg, 2 mmol) and 4-(dimethylamino)pyridine (122 mg, 1 mmol). The mixture was stirred at room temperature for 24 hours. The course of the reaction was monitored by thin-layer chromatography (silica gel 60 $F_{254}$, Merck, hexane-acetone 3:2). The reaction was quenched with water (1 ml), evaporated to dryness in vacuum. The residue was dissolved in chloroform, and the solution was washed with saturated sodium bicarbonate solution, brine, dried over $Na_2SO_4$ and evaporated. The residue was dried by co-evaporation with pyridine and finally dissolved in 10 ml of dry pyridine. To the solution were successively added 2,4,6-triisopropylbenzenesulfonyl chloride (1.6 g, 5.5 mmol) and long-chain amino-CPG (Millipore, 500 Å, amino groups 160 umol/g). The mixture was shaken for one hour. The CPG was washed with acetonitrile, residual unreacted amino-groups were capped by treatment with 20 ml of a mixture of acetic anhydride-pyridine-N-methylimidazole-tetrahydrofuran (1:1:1.5:16.5) for 10 min. Obtained CPG-modifier (I; Met=b, n=5, m=2) was rinsed with methanol, acetonitrile and acetone and dried in vacuum. The loading was determined by DMTr-cation assay procedure as described in [8] and consisted 45-60 umol/g.

5. Methacylamide modifier phosphoramidite (II, Met=b, n=5). To a solution of (4, Met=b, n=5) (575 mg, 1 mmol) in anhydrous dichloroethane (10 ml) was added 1H-tetrazole (70 mg, 1 mmol) and 2-cyanoethyl tetraisopropylphosphoramidite (330 mg, 1.1 mmol). The resulting mixture was stirred for 1 hour, dichloroethane (20 ml) was added and the solution was washed with saturated solution of sodium bicarbonate (3×20 ml), and brine (2×20 ml). The organic phase was dried over $Na_2SO_4$, and the solvent was evaporated to approximate volume 1 ml. This solution was added drop wise to hexane (100 ml) at −10° C. The supernatant was pouring off, the oil residue was dissolved in acetonitrile, evaporated and dried in vacuum over $P_2O_5$ to give 620 mg (90%) of the title compound.

Synthesis of Metacrylamido-Modified Oligonucleotides.

Oligonucleotide synthesis was carried out on an AB 394 DNA/RNA synthesizer (Applied Biosystems US) 1 mmol scale using phosphoramidite chemistry. The cleavage of oligonucleotides from the CPG and removing of protecting groups were performed following the standard procedure. After HPLC purification the products were characterized by MALDI-TOF MS.

Methacrylamido-modifiers CPG (I, see FIG. 2) were used as a solid phase for synthesis of set of oligonucleotides containing methacrylic function at 3'-ends. 0.1M solution of phosphoramidite (II, see FIG. 2) in acetonitrile were used according the standard conditions of the reaction cycle for phosphoramidite chemistry for the incorporation of methacrylamide function at 5'-end or at internal position of oligonucleotides.

C. Fabrication of Copolymerization Microarrays

Copolymerization microarrays were printed on plain microscope slides (Cat. No. 12-544-1, Fisher Scientific, Pittsburgh, Pa.) using technique as described in [6]. The slides were prepared for printing according the following protocol: (a) immerse in 5 M sodium hydroxide solution for 30 minutes; (b) rinse five times with double-distilled water; (c) immerse in concentrated sulfuric acid in for 30 minutes; (d) rinse five times with double-distilled water; (e) air dry for 1 hour. After the cleaning, the slides were immersed in 5% solution of 3-(Trimethoxysilyl)propyl methacrylate (Aldrich, Saint Louis, Mo.) in dichloromethane, incubated for 40 min at room temperature, thoroughly rinsed with ethanol, double-distilled water, and finally dried in a flow of nitrogen.

Solutions for copolymerization contained 5%(w) acrylamide, 0.25%(w) methylenebisacrylamide, 65%(w) glycerol, 0.035M sodium phosphate buffer (pH 7.25), 0.25 mM methacrylated oligonucleotides.

Copolymerization mixtures were printed with a QArray2 arrayer (Genetix, New Milton, UK) using four "solid" 150 μm pins. On completion of printing, the slides were incubated overnight in an airtight container with 2 to 4 ml of a mixture that included all the components of the mixture used for printing the arrays except the oligonucleotides. After the incubation, the slides were placed in an airtight cassette equipped with quartz windows and polymerized for 30 min in a nitrogen atmosphere under a Thermo Spectronic Model XX-15A UV lamp (Cat. No. 11-982-120, Fisher Scientific, Pittsburgh, Pa.) with 312 nm tubes Model FB-T1-110A (Fisher Scientific). Finally, the slides were transferred to an ArrayIt™ High-Throughput Wash Station (Telechem International, Sunnyvale, Calif.) filled with 400 ml of 0.01 M SSPE washing buffer (Ambion, Austin, Tex.), washed for 1 hour on a Nuova stirring hot plate (Barnstead/Thermolyne, Dubuque, Iowa), thoroughly rinsed with MilliQ water, and air dried.

PUBLICATIONS CITED

These publications are incorporated by reference to the extent they relate materials and methods for the practice of the claimed invention,
Claus, B. V. et al. Talanta, 2002, 56, 280-299.
Farah, N. et al. Nucleic Acids Res., 1999, 27, 649-655.
Vasiliskov V. A. et al. Biotechniques, 1999, 27, 592-606.
Mirzabekov A. D. et al. Russian Patent N2175972, 2001.
Mirzabekov A. D. et al. Patent WO 03/010203.
Rubina, A. Yu. et al. Analytical Biochemistry, 2004, 325, 92-106.
US Patent Application Publication 2004/0086866A1.
Roland, A. et al., (2001) Tetrahedron Letters, 42:3669-3672.

4. The compound of claim 1 wherein $Q^1$ is an oligonucleotide attached at the 5'-end.

5. The compound of claim 1 wherein $Q^2$ is an oligonucleotide attached at the 3'-end.

6. The compound of claim 1 wherein $Q^1$ and $Q^2$ are each an independently selected oligonucleotide.

7. The compound of claim 1 wherein $Q^1$ is an oligonucleotide attached at the 5'-end and $Q^2$ is an oligonucleotide attached at the 3'-end.

8. The compound of claim 1 wherein $L^2$ is a single bond; and $Q^2$ is a hydroxyl protecting group.

9. The compound of claim 1 wherein the hydroxyl protecting group is an optionally substituted trityl group.

10. The compound of claim 1 wherein $L^1$ is a linker formed from a dicarbonic acid fragment.

11. The compound of claim 1 wherein the dicarbonic acid fragment is a fragment of aliphatic dicarbonic acid of the formula:

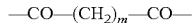

wherein m is an integer from 0 to about 8.

We claim:
1. A compound of the formula

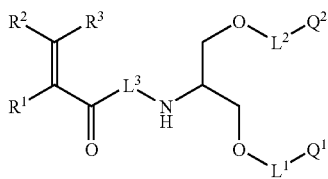

wherein
$R^1$, $R^2$, and $R^3$ are each independently selected from the group consisting of hydrogen, alkyl;
$L^1$, $L^2$, and $L^3$ are each independently selected from the group consisting of a single bond, and a linker; and
$Q^1$ and $Q^2$ are each independently selected from the group consisting of hydrogen, a hydroxyl protecting group, a phosphoramidite group, an oligonucleotide, a solid support, and combinations thereof.

2. The compound of claim 1 wherein $R^1$ is hydrogen or alkyl; and $R^2$ and $R^3$ are each hydrogen.

3. The compound of claim 1 wherein $L^3$ is a linker selected from the group consisting of ω-amino acid fragments of the formula

wherein n is an integer from 2 to about 12.

12. The compound of claim 1 wherein $L^1$ is a linker formed from a dicarbonic acid fragment; and $Q^1$ is a solid support.

13. A reagent for forming a compound of any one of claims 1 to 12, said reagent of the formula

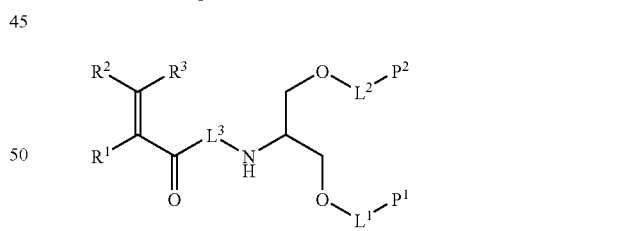

wherein
$R^1$, $R^2$, and $R^3$ are each independently selected from the group consisting of hydrogen, alkyl;
$L^1$, $L^2$, and $L^3$ are each independently selected from the group consisting of a single bond, and a linker; and
$P^1$ and $P^2$ are each independently selected from the group consisting of hydrogen, a hydroxyl protecting group, a phosphoramidite group, a solid support, and combinations thereof.

14. The compound of claim 13 wherein $P^1$ is a cyanoethylphosphoramidite coupling group.

15. The compound of claim 13 wherein $P^1$ is a solid support.

16. The compound of claim 13 wherein $L^1$ is a linker; and $P^1$ is a solid support.

17. The compound of claim 13 wherein the linker is a fragment of aliphatic dicarbonic acid of the formula:

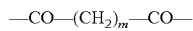

wherein m is an integer from 0 to about 8; and the linker is covalently attached to the solid support by nitrogen of amino group.

18. A method for preparing a biochip, the method comprising the steps of:
   (a) placing a mixture comprising (i) a compound of claim 1 and (ii) gel forming monomers, or analogs or derivatives thereof on a solid support; and
   (b) polymerizing the mixture.

19. The method of claim 18, wherein the gel forming monomers are acrylamide or/and methacrylamide.

20. The method of claim 18, wherein the placing step includes placing the mixture on the solid support in the form of a drop.

* * * * *

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
taacttcata agagcaagcc t                                           21